United States Patent [19]

Oude Alink et al.

[11] 4,387,074
[45] Jun. 7, 1983

[54] POLYOLS OF TETRAHYDROPYRIMIDINES AS CORROSION INHIBITORS

[75] Inventors: Bernardus A. Oude Alink, St. Louis; Benjamin T. Outlaw, Webster Groves, both of Mo.

[73] Assignee: Petrolite Corporation, St. Louis, Mo.

[21] Appl. No.: 336,145

[22] Filed: Dec. 31, 1981

Related U.S. Application Data

[62] Division of Ser. No. 81,748, Oct. 4, 1979, Pat. No. 4,343,941.

[51] Int. Cl.$^3$ .................. C07D 239/06; C23F 11/04; C23F 11/12; C23F 11/14
[52] U.S. Cl. ................................ 422/12; 252/390; 422/7; 422/16; 544/242; 544/335
[58] Field of Search ............... 422/7, 12, 16; 544/242, 544/335; 252/390

[56] References Cited

U.S. PATENT DOCUMENTS

| | | | |
|---|---|---|---|
| 2,516,626 | 7/1950 | Haury .................................. | 544/242 |
| 3,205,232 | 9/1965 | Andress et al. ...................... | 544/242 |
| 3,502,578 | 3/1970 | Raifsnider et al. .................. | 544/335 |
| 3,673,186 | 6/1972 | Cyba .................................... | 544/335 |
| 3,787,416 | 1/1974 | Cyba .................................... | 544/335 |
| 3,926,994 | 12/1975 | White et al. ........................ | 544/242 |
| 4,145,545 | 3/1979 | Oude Alink ........................ | 544/242 |
| 4,174,370 | 11/1979 | Oude Alink et al. ................ | 422/12 |
| 4,212,843 | 7/1980 | Oude Alink ........................ | 422/12 X |

Primary Examiner—Barry S. Richman
Attorney, Agent, or Firm—Sidney B. Ring; Hyman F. Glass

[57] ABSTRACT

Methylol derivatives of 2,3,4,5-tetrahydropyrimidines and to uses thereof, particularly as corrosion inhibitors.

7 Claims, No Drawings

POLYOLS OF TETRAHYDROPYRIMIDINES AS CORROSION INHIBITORS

This is a division of application Ser. No. 81,748, filed Oct. 4, 1979, now U.S. Pat. No. 4,343,941, issued Aug. 10, 1982.

In U.S. Pat. No. 4,145,545 there is described and claimed a method of preparing Substituted 2,3,4,5-tetrahydropyrimidines (THP) of the formula

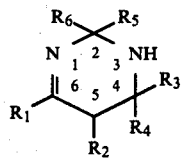

where $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition, the R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula $$(CH_2)_n C=O$$

such as cyclohexanone, cyclopentanone, substituted derivatives thereof such as alkyl-cyclohexanone, dialkyl-cyclohexanone, etc.

We have now discovered that the THP's prepared in U.S. Pat. No. 4,145,545 can be reacted with an aldehyde such as formaldehyde to yield methylol derivatives of THP.

The reaction is carried out by reacting the THP with formaldehyde under conditions which produce the desired product. In practice aqueous formaldehyde (formalin) is employed. The reaction is carried out at about room temperature or higher, such as from about 25° to 140° C., for example from about 25° to 70° C., but preferably from about 25° to 40° C.

The stoichiometric ratio of THP to formaldehyde can vary widely from about 1 to 6, such as from about 1 to 5, but preferably from about 1 to 4.

In general, one employs at least one mole equivalent of formaldehyde for each mole equivalent one desires to be present in the derivative. Thus, if one desires the derivative to have 1 methylol group the ratio of formaldehyde to THP is at least 1; two methylol groups, the ratio is at least 2; three methylol groups the ratio is at least 3; 4 methylol groups the ratio is at least 4, etc. At ratios of less than 4/1, a large variety of methylol derivatives are obtained. The most favored reaction sites being the 3 position (i.e. N—H) and the methyl group ($CH_3$) at the 6 position.

The following Table A presents typical examples of THP's prepared in U.S. Pat. No. 4,145,545 which can be reacted in accord with the present invention:

TABLE A

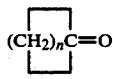

| | Ring Position | | | | |
|---|---|---|---|---|---|
| | 6 | 5 | 4 | 4   2 | 2 |
| | Subst. Group | | | | |
| Ex. | $R_1$ | $R_2$ | $R_3$ | $R_4$    $R_5$ | $R_6$ |
| 1 | $CH_3$ | H | $CH_3$ | $CH_3$    $CH_3$ | $CH_3$ |
| 2 | $CH_3$ | H | $CH_3$ | $CH_3$    H | $CH_3$ |
| 3 | $CH_3$ | H | $CH_3$ | $CH_3$    H | $n\text{-}C_3H_7$ |
| 4 | $CH_3$ | H | $CH_3$ | $CH_3$    H | $n\text{-}C_6H_{13}$ |
| 5 | $CH_3$ | H | $CH_3$ | $CH_3$    H | $i\text{-}C_5H_{11}$ |
| 6 | $CH_3$ | H | $CH_3$ | $CH_3$    H | Phenyl |
| 7 | $CH_3$ | H | $CH_3$ | $CH_3$    H | $i\text{-}C_7H_{15}$ |
| 8 | $CH_3$ | H | $CH_3$ | $CH_3$    H | $n\text{-}C_8H_{17}$ |
| 9 | $CH_3$ | H | $CH_3$ | $CH_3$    H | $CH_3$ |
| 10 | $CH_3$ | H | $CH_3$ | $CH_3$    H | $CH_3$ |
| 11 | $CH_3$ | H | $CH_3$ | $CH_3$    H | $C_2H_5$ |
| 12 | $CH_3$ | H | $CH_3$ | $CH_3$    $—(CH_2)_5—$ | |
| 13 | $CH_3$ | H | $CH_3$ | $CH_3$    $—(CH_2)_2—C(CH_3)—(CH_2)_2—$ | |
| 14 | $CH_3$ | H | $CH_3$ | $CH_3$    $—(CH_2)_5—$ | |

In the present process, it is preferred that $R_2$ be hydrogen so that substitution can occur at this position. Large R groups in the 2 position (i.e. $R_5$ and $R_6$) such as those having 3 or more carbons for example

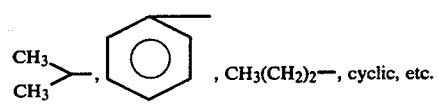

tend to impede substitution in the 3-position (i.e. NH).

The following equation illustrates the reactions of the present invention:

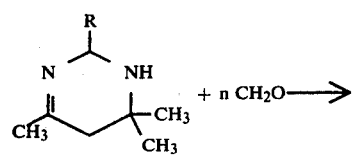

I a–d

-continued

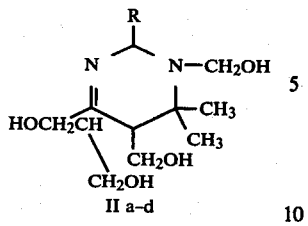
II a-d

In the above equation n=4.
Specific illustrations include the following:

|   | I a-e |   | II a-e |   |
|---|---|---|---|---|
|   | R₁ | R₂ | R₁ | R₂ |
| a | H | H | H | H |
| b | CH₃⟩CH₃ | H | CH₃⟩CH₃ | H |
| c | CH₃CH₂CH₂— | H | CH₃CH₂CH₂— | H |
| d | ⌬ | H | ⌬ | H |
| e | R₁ + R₂ = —(CH₂)₅ |   | R₁ + R₂ = —(CH₂)₅ |   |

Reaction where n is less than 4 produces mixtures with the —CH₂OH group located at one or more of the four possible reaction sites 3, 5, and 6 (one or two CH₂OH's on the methyl group). Large R-substituents at position 2 usually hinder reaction at the 3 position (—NH).

The following examples are presented for purposes of illustration and not of limitation.

EXAMPLE 1

4,4,6-Trimethyl 2,3,4,5-tetrahydropyrimidines

In a 2 liter three necked round-bottom flask equipped with a mechanical stirrer, a thermometer, and a reflux condenser was charged a mixture of 196.3 g of mesityl oxide and 400 ml. of concentrated ammonium hydroxide. The mixture was stirred at room temperature for 18 hours. To this mixture was added 162.3 g of 37% formaldehyde (in H₂O) over 20 minutes. An ice-water bath was used to maintain the reaction temperature at 40°. This mixture was stirred at room temperature for 18 hrs. The excess ammonia was removed by distillation under reduced pressure. The remaining liquid was distilled to yield 176.7 g (68.5% of theory) of 4,4,6-trimethyl-2,3,4,5-tetrahydropyrimidine. $^{13}$C NMR (solvent CDCl₃), δ in ppm, internal standard t.m.s.

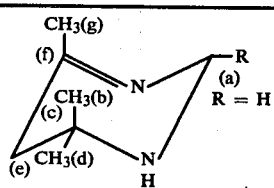

| a. | 61.29 |
| b. | 27.66 |
| c. | 45.91 |
| d. | 27.66 |
| e. | 42.14 |
| f. | 27.66 |
| g. | 164.73 |

% N Calc. 22.22; Found 19.36.
In a similar manner products were made where

R = 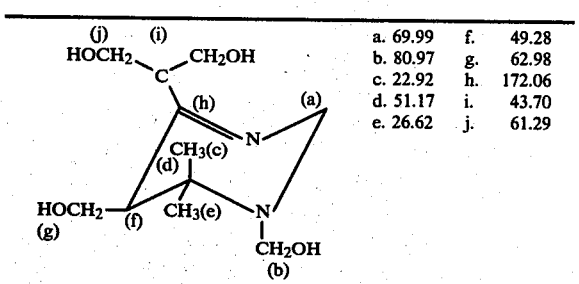

EXAMPLE 2

Reaction of product from example 1 (R=H, Ia) with formaldehyde. In a 200 ml three-necked flask equipped with a mechanical stirrer, a thermometer, and a reflux condenser was charged 20 g Ia and 51.4 g of 37% formaldehyde solution. The mixture was stirred at room temperature for 5 hrs. The solvent was removed by distillation under reduced pressure, to yield 33.2 g of a very viscous liquid (84.6% of theory). $^{13}$C NMR (solvent CDCl₃), δ in ppm, internal standard t.m.s.

| a. | 69.99 | f. | 49.28 |
| b. | 80.97 | g. | 62.98 |
| c. | 22.92 | h. | 172.06 |
| d. | 51.17 | i. | 43.70 |
| e. | 26.62 | j. | 61.29 |

% N: Calc. 11.38; Found 11.85.
The product is a result of 4 moles formaldehyde reacting with the tetrahydropyrimidine.

EXAMPLE 3

In a similar manner to that in example 2, tetrahydropyrimidine, Ia (20 g) was reacted with 38.6 g of 37% formaldehyde (¾ molar ratio) 36.2 g of viscous liquid was obtained (87.7% of theory). A mixture of products are possible containing three methylol groups.

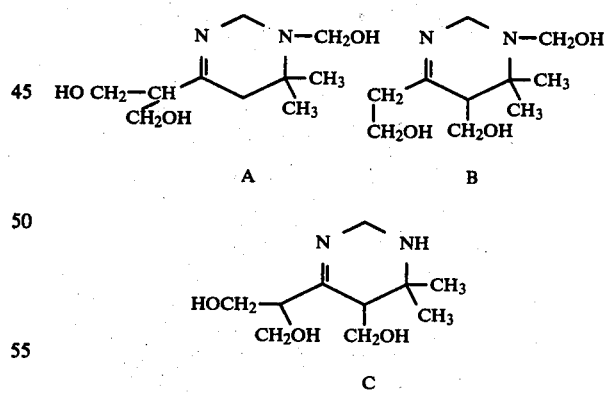

$^{13}$C NMR data favors structure A as the major product.
% N: Calc. 12.96; Found 14.09.

EXAMPLE 4

In a similar manner to that in example 2, tetrahydropyrimidine Ia (20 g) was reacted with 25.9 g of 37% formaldehyde (½ molar ratio). 25.3 g of viscous liquid product (85.4% of theory) was obtained. Again a mixture of products are possible.
% N: Calc. 15.05; Found 16.06.

[Structures A, B, C shown at top of page:

A: tetrahydropyrimidine ring with N—CH₂OH, CH₂/CH₂OH substituent, and C(CH₃)₂

B: similar ring with CH₃, CH₃/CH₂OH, and C(CH₃)₂—CH₂OH substituents

C: ring with NH, CH₂/CH₂OH, and C(CH₃)₂—CH₂OH]

EXAMPLE 5

In a similar manner to example 2, tetrahydropyrimidine, Ia (20 g) was reacted with 13 g of 37% formaldehyde (1/1 molar ratio). 20.8 g of viscous liquid product (83.9% of theory) was obtained. Possible products are:

[Structures A, B, C shown: variants of tetrahydropyrimidine with CH₂OH, CH₃ groups]

% N Calc. 17.45; Found 18.91.

EXAMPLE 6

In a similar manner to example 2, tetrahydropyrimidine Ib $$(R = \begin{array}{c} CH_3 \\ CH_3 \end{array}\!\!\!>\!\!-)$$

(33.6 g) was reacted with 64.9 g of 37% formaldehyde (¼ molar ratio). 50.4 g (87.5% of theory) of viscous product was obtained.

% N: Found 9.70; % N: Calc. 3:1 polyol 10.85, 4:1 polyol 9.72.

EXAMPLE 7

In a similar manner to example 2, tetrahydropyrimidine, Ic (R=CH₃CH₂CH₂—) (100 g) was reacted with 194.8 g of 37% formaldehyde (¼ molar ratio). 154.6 g of viscous product (89.8% of theory) was obtained.

% N: Found 9.90; % N: Calc. 3/1 polyol 10.85, 4/1 polyol 9.72.

EXAMPLE 8

To a 500 ml. three-neck flask equipped with a mechanical stirring thermometer, and reflux condenser was charged 101 g of tetrahydropyrimidine, Ic $$(R = \phantom{xx}\bigcirc\phantom{xx}),$$

162.3 g of 37% formaldehyde, and 100 ml of isopropyl alcohol. After 16 hrs. of stirring at room temperature the solvent was removed by distillation under reduced pressure. 136.7 g of viscous liquid (84.7% of theory) was obtained.

% N: Found 8.57; % N: Calc. 3/1 polyol 9.59, 4/1 polyol 8.69.

EXAMPLE 9

In a similar manner to example 2, tetrahydropyrimidine, Ie (R₅+R₆=—(CH₂)₅—) (20.3 g) treated with 36.8 g of 37% formaldehyde (¼ molar ratio) to yield a viscous product.

Main product, structure found to be as follows:

[Structure: cyclohexane spiro-fused to tetrahydropyrimidine ring with N, NH, CH₃, CH₃ groups and HOCH₂—CH, CH₂OH, CH₂ substituents]

The above product is the result of a dehydration reaction of the methylol group in the 5-position under the reaction conditions used.

EXAMPLE 10

In a similar manner to example 2, Ie (20 g) was treated with 16.2 g of 37% formaldehyde to yield a viscous product. (¼ molar ratio).

EXAMPLE 11

In a similar manner to example 2, Ie (20 g) was treated with 8.1 g of 37% formaldehyde to yield a viscous product (1/1 molar ratio).

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oil-base drilling fluids comprising, for example a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as sulfuric acid; Turkey-red oil; soaps of fatty acids, for example, sodium oleate; emulsoid colloids, for example, starch, sodium alginate, etc. Varying amounts of finely divided clay, silica, calcium carbonate, blown asphalt and other materials may be added to these emulsions to improve their properties and control their weight.

The compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hold and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling but is indispensible in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressure of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The amount of the composition of the invention to be employed as a corrosion inhibitor can vary widely depending upon particular compounds, the particular system, the amounts of oxygen present, etc. We may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injections well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals. We have now discovered a method of preventing corrosion in systems containing a corrosive aqueous media, and most particularly in systems containing brines, which is characterized by employing the compositions of this invention.

We have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analagous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 1,000 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

USE IN ACID SYSTEMS

The compounds of this invention can also be employed as corrosion inhibitors for acid systems, for example as illustrated by the pickling of ferrous metals, the treatment of calcareous earth formations, etc., as described in the following sections.

USE AS PICKLING INHIBITORS

This phase of the invention relates to pickling. More particularly, the invention is directed to a pickling composition and to a method of pickling ferrous metal. The term "ferrous metal" as used herein refers to iron, iron alloys and steel.

To prepare ferrous metal sheet, strip, etc. for subsequent processing, it is frequently desirable to remove oxide coating, formed during manufacturing, from the surface. The presence of oxide coating, referred to as "scale" is objectionable when the material is to undergo subsequent processing. Thus, for example, oxide scale must be removed and a clean surface provided if satisfactory results are to be obtained from hot rolled sheet and strip in any operation involving deformation of the product. Similarly, steel prepared for drawing must possess a clean surface and removal of the oxide scale therefrom is essential since the scale tends to shorten drawing-die life as well as destroy the surface smoothness of the finished product. Oxide removal from sheet or strip is also necessary prior to coating operations to permit proper alloying or adherence of the coating to the ferrous metal strip or sheet. Prior to cold reduction, it is necessary that the oxide formed during hot rolling be completely removed to preclude surface irregularities and enable uniform reduction of the work.

The chemical process used to remove oxide from metal surfaces is referred to as "pickling." Typical pickling processes involve the use of aqueous acid solutions, usually inorganic acids, into which the metal article is immersed. The acid solution reacts with the oxides to form water and a salt of the acid. A common problem in this process is "overpickling" which is a condition resulting when the ferrous metal remains in the pickling solution after the oxide scale is removed from the surface and the pickling solution reacts with the ferrous base metal. An additional difficulty in pickling results from the liberated hydrogen being absorbed by the base metal and causing hydrogen embrittlement. To overcome the aforementioned problems in pickling, it has been customary to add corrosion inhibitors to the pickling solution.

The present invention avoids the above described problems in pickling ferrous metal articles and provides a pickling composition which minimizes corrosion, overpickling and hydrogen embrittlement. Thus the pickling inhibitors described herein not only prevent excessive dissolution of the ferrous base metal but effectively limit the amount of hydrogen absorption thereby during pickling. According to the invention, a pickling composition for ferrous metal is provided which comprises a pickling acid such as sulfuric or hydrochloric acid and a small but effective amount of the compounds of this invention, for example at least about 5 p.p.m., such as from about 100 to 10,000 p.p.m., but preferably from about 3,000 to 7,000 p.p.m.

Ferrous metal articles are pickled by contacting the surface (usually by immersions in the pickling solution) with a pickling composition as described to remove oxide from their surface with minimum dissolution and hydrogen embrittlement thereof and then washing the ferrous metal to remove the pickling composition therefrom.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oilbearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

These compounds were tested as HCl Pickle acid corrosion inhibitors according to the following procedure:

HCl Pickle Acid Test Procedure

I. Equipment
 Oil Bath—capable of maintaining 200° F.;
 Analytical Balance;
 300 ml beakers;
 $\frac{7}{8} \times 3\frac{1}{4} \times 1/6$ 1020 mild steel coupons;
 HCl pickle Acid;
 Watch glasses
 HCl Pickle Acid
 To 500 ml of tap water, add 135 ml of reagent grade (37%) HCl. Then dissolve 240 g $FeCl_2$–$4H_2O$. Dilute to 1 liter with tap water. (This is *about* 5% HCl and 7% Fe).

II. Procedure
 Preheat oil bath to 190° F.;
 Put 200 ml of HCl Pickle Acid in a 300 ml beaker and then place in oil bath. Leave acid in oil bath for one (1) hour so that the acid is at the correct temperature.
 Add chemical to be tested. The standard concentration used is 0.25% (0.5 ml of inhibitor/200 ml acid); however, this can be changed at the discretion of the tester.
 Clean the coupons by immersing briefly (5–10 seconds) in 15% HCl, then in hot water, then in hot acetone and air dry.
 Weigh coupons;
 Place coupons in test beakers at 30 second intervals. Let corrode for exactly one (1) hour.
 Note test details—foaming, gas evolution, etc.
 Remove coupons at 30 second intervals in original sequence. Immediately on removal from test beaker, wash coupon in hot water to remove the acid, then in hot acetone, then air dry. (The thirty (30) second interval should allow plenty of time for this).
 Reweigh coupons.

$$\% \text{ Protection} = \frac{\text{Blank weight loss} - \text{Test Weight Loss}}{\text{Blank Weight Loss}} \times 100$$

Typical results are presented in the following table.

| 0.25% Concentration of Inhibitor | |
| --- | --- |
| Inhibitor | % Protection |
| Ex. 3 | 94.3 |
| Ex. 4 | 94.0 |
| Ex. 5 | 93.3 |

We claim:
1. A process of inhibiting corrosion of metal in contact with a water-containing corrosive medium which comprises adding to said medium a corrosion-inhibiting amount of at least one methylol derivative of 2,3,4,5-tetrahydropyrimidines where there is a methylol substitution at two or more of the following positions:
 (1) the ring-N at the 3 position;
 (2) the ring carbon at the 5 position; and

(3) 1 or 2 hydrogens of the α-methyl group at the 6 position.

2. The process of claim 1 wherein the methylol derivative of 2,3,4,5-tetrahydropyrimidine is

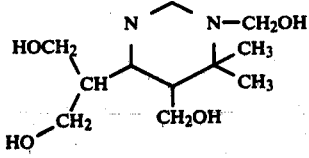

3. The process of claim 1 wherein the 2,3,4,5-tetrahydropyrimidines prior to methylolation have the formula

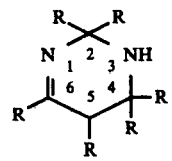

where the R's which may be the same or different, are hydrogen or a substituted group.

4. The process of claim 3 wherein the R's are hydrogen or hydrocarbon group.

5. The process of claim 4 wherein the R's are hydrogen or alkyl.

6. The process of claim 5 wherein the alkyl is methyl.

7. The process of claim 6 wherein the tetrahydropyrimidine prior to methylol substitution has the formula

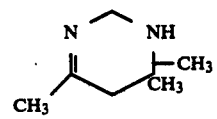

* * * * *